United States Patent [19]

Refojo et al.

[11] Patent Number: 4,461,303
[45] Date of Patent: Jul. 24, 1984

[54] NON-INTRUSIVE TEAR EVAPORIMETER

[75] Inventors: Miguel F. Refojo, Lexington, Mass.; Maurizio Rolando, Genoa, Italy

[73] Assignee: Eye Research Institute of Retina Foundation, Boston, Mass.

[21] Appl. No.: 372,814

[22] Filed: Apr. 28, 1982

[51] Int. Cl.³ .............................................. A61B 5/00
[52] U.S. Cl. .................................... 128/630; 128/632; 73/29
[58] Field of Search ........................ 128/163, 630, 632; 73/29

[56] References Cited

U.S. PATENT DOCUMENTS 3,139,085 6/1964 Custance et al. .................... 128/630
3,318,302 5/1967 Adams ................................. 128/630
4,066,068 1/1978 Nilsson et al. ....................... 128/630
4,303,063 12/1981 Stahl ................................ 128/163 X
4,398,543 8/1983 Sandlin et al. ................... 128/749 X Primary Examiner—Kyle L. Howell
Assistant Examiner—Christine A. Fukushima
Attorney, Agent, or Firm—Lahive & Cockfield

[57] ABSTRACT

The non-intrusive measurement of preocular tear film evaporation employs a goggle fitted on a subject and connected with apparatus for introducing air of known conditions to a goggle chamber over one eye, apparatus for controlling air movement within the goggle chamber, and apparatus for humidity measurement of the chamber air.

A measure of palpebral aperture readily provides the area of the exposed eye surface, for calculating the rate of tear evaporation.

19 Claims, 3 Drawing Figures

NON-INTRUSIVE TEAR EVAPORIMETER

BACKGROUND OF THE INVENTION

This invention relates to a method and apparatus for the non-invasive measurement of the evaporation of the aqueous tear film from the front surface of the eye. The invention also provides a new measure of exposed surface area of an eye.

The eye of humans, as well as other animals, is normally covered by a tear film. An unstable or deficient tear film can cause ocular discomfort and more severe afflictions of the conjunctival and corneal surfaces. The eye loses tear fluid by various mechanisms, including outflow through the puncta and evaporation.

The tear film is subject to evaporation, which can reduce the thickness of the tear film, whenever it is exposed to air of less than one hundred percent relative humidity. This evaporative reduction in thickness prompts the often-used clinical measurement of tear breakup time. However, a consistent measure of tear film evaporation has not been available. Rather, different investigators working with rabbits and using various techniques have reported widely varying evaporation rates, namely from 7.8 to 41.6, the measurements being in the units $10^{-7}$ gm/cm$^2$/sec. One prior report for evaporation from the precorneal tear film of a human eye was 27 such units. In contrast, apparatus according to this invention consistently indicates that the evaporation rate from an eye of a healthy human is approximately 4, whereas that of a pathologic human is in the order of 8, using the same units.

One investigator, Von Bahr in 1941, determined the amount of water vapor uptake by circulating dry air in a chamber that was attached by suction to the corneal surface of a rabbit eye. (Konnte der Flussigkeitsabgang durch die Cornea von physiologischer Bedeutung sein?, *Acta Ophthalmol.* 19, 125–34, von Bahr, G. (1941)) Mishima and Maurice in 1961 calculated the evaporation rate from the precorneal tear film of rabbits from measurements of corneal thickness and made with the anterior eye chamber filled with oil. (The oily layer of the tear film and evaporation from the corneal surface., *Exp. Eye Res.*, 1, 39–45, Mishima, S. and Maurice, D. M. (1961)) Iwata, Lemp, Holly and Dohlman in 1969 studied evaporation from the precorneal tear film and the corneal surfaces of rabbit eyes by sealing a chamber of polymethylmethacrylate on the cornea, and measuring the water vapor taken up by dry air passed through the chamber during a given time period. (Evaporation rate of water from the precorneal tear film and cornea in the rabbit., *Invest. Ophthalmol. Vis. Sci.*, 8, 613–9, Iwata, S., Lemp, M. A., Holly, F. J. and Dohlman, C. H. (1969)). In a 1980 study, Hamano, Hori, and Mitsunaga used a modified dermatologic evaporimeter that operates on the basis of the law of water diffusion into air from a surface. (Application of an evaporimeter to the field of ophthalmology., *J. Jpn. Contact Lens Soc.*, 22, 101–7, Hamano, H., Hori, M. and Mitsunaga, S. (1980)). The Hamano et al experiments involved touching the tear film or the corneal surface. It is considered highly likely, however, that any such contact would interfere significantly with the delicate and unstable structure of the tear film.

It accordingly is an object of this invention to provide a method and apparatus for measuring preocular tear evaporation with precision and accuracy.

A further object of the invention is to provide for the measurement of tear evaporation non-intrusively and non-invasively, i.e. without introducing any instrument or foreign substance to the tear film or the corneal surface.

A more specific object of the invention is to provide a method and apparatus for the foregoing measurement in both normal and pathologic cases under controlled reproducible, physiological conditions and without the disadvantage of any stimulus or perturbation causing irritation, blinking or other alteration of the tear film structure.

It is a further object of the invention to provide an improved measure of the area of an exposed, i.e. open, eye surface. A further aspect of this object is to provide such a measure non-intrusively and non-invasively and, moreover, in a way that is easily practiced.

Other objects of the invention will in part appear hereinafter and will in part be obvious.

SUMMARY OF THE INVENTION

According to features of the invention, a chamber substantially closed to the environment is formed over the eye being measured. After a period of evaporation into the chamber from the eye, the air within the chamber is mixed and exposed to a sensing element for measuring parameters that identify the relative humidity. A further feature is that the air within the chamber is free of applied flow during the evaporation period. This provision of a non-flowing condition of the air during the evaporation period coupled with mixing of the air prior to sensing enhances precise measurements.

One preferred instrument for the practice of the invention employs a goggle-like cup which forms the closed chamber over the eye being measured. An inlet conduit connects a motive element such as a pump to introduce air into the preocular chamber and an outlet conduit feeds air from within the chamber to an element for sensing humidity and temperature. A valve allows air of selected temperature and humidity to be pumped into the chamber to provide initializing base line conditions prior to measurement, allows the conduits to be essentially closed from external disturbances—to allow the air within the chamber to be stationary—during a period in which the tear film is allowed to evaporate into the chamber, and, further, allows the air within the chamber to be circulated through the outlet and inlet conduits to effect the foregoing mixing. This mixing circulation of the air after the evaporation period exposes the sensing element to the mixed air, for providing the post-evaporation measurement. Comparison with a similar measurement made prior to the evaporation period yields an accurate measure of a humidity change due to tear film evaporation.

It further has been found that a measure of the height of a person's palpebral opening, i.e. of the palpebral aperture, correlates closely with the area of the exposed eye surface. This is the surface from which tear film evaporation takes place. An instrument according to the invention accordingly further includes a vertical scale on a lens of the chamber-forming goggle-like cup. A measure of palpebral aperture made with this scale readily converts to the area of a subject's exposed eye surface. This area measurement is used in computing evaporation rate from the foregoing measure of the change in humidity.

More particularly, the measuring procedure which the invention provides commences with the application of a substance such as petroleum jelly to the skin surrounding the eye being measured, for the purpose of minimizing evaporation from the lids and the orbital region. The goggle-like chamber-forming cup is placed on the subject over the eye being measured. The subject closes the eye to be examined and an air pump introduces air of known temperature and humidity to the chamber until a desired base line relative humidity is attained. This preparatory operation continues until the air in the goggle-formed chamber and in the external conduits and pump are brought to constant relative humidity.

The subject then opens the eye and endeavors to hold it open with constant palpebral aperture, as by staring straight ahead without blinking, for a selected evaporation interval. The interval typically is of the order of a minute, although different times can be used under different conditions and with instruments of different sensitivity. During this period, water evaporates from the tear film, over the exposed eye surface, into the air within the chamber. The evaporation takes place under controlled conditions and in the absence of external non-physiologic stimuli. Also, the palpebral aperture, i.e. the lid aperture, during the evaporation interval is measured against the scale carried on the lens of the goggle cup.

Upon termination of the selected evaporation interval, the subject again closes the eye and the pump is activated to circulate the air within the eye chamber through the inlet and outlet conduits, thereby mixing the air within the chamber, as well as mixing it with the air in the closed volume that includes the chamber and the inlet and outlet conduits and the pump. The sensing element is exposed to the new equilibrium level of humidity of the mixed air to provide a measure of the resultant relative humidity.

The tear evaporation rate of the subject's eye can be calculated from the data measured during the foregoing procedure in the following manner. The difference in relative humidity (RH) as measured immediately prior to the evaporation interval, RH1, and immediately thereafter, RH2, yields an increase in relative humidity, RH(2-1), due to the evaporation being measured:

$$RH(2-1) = RH2 - RH1 \quad (1)$$

Relative humidity is the ratio between the concentration of water vapor in the system (C) and the concentration of saturated water vapor at the temperature of the system (Co). Thus, $$RH = C/Co \quad (2)$$

The water evaporation from the tear film, E, in grams per square centimeter per second can accordingly be calculated according to the following equation:

$$E = \frac{(C2 - C1)V}{At} \quad (3)$$

where:
C1 in grams per milliliter is the water vapor concentration immediately prior to the evaporation period and at the temperature of the measurement, as determined from the measured value of the initial relative humidity, RH1, by using equation 2;
C2 in grams per milliliter is the water vapor concentration at the end of the evaporation period as determined from the measured value of the final relative humidity, RH2, by using Equation 2;
V in milliliters is the volume of the system in which the evaporation takes place and the air is mixed and sensed, e.g. is the volume of the chamber which the goggle device forms over the eye being measured plus the volume of the air-circulating pump and conduits and sensor housing;
t in seconds is the duration of the evaporation interval; and
A in square centimeters is the area of the exposed eye surface during the evaporation interval.

The area of the exposed surface of the eye can be measured photographically to provide the quantity A for equation 3. In this practice, the eye is photographed through the goggle during the evaporation interval. The area of the photographed image can be measured with any of known practices including with a planimeter or a calculator-plotter. The diameter of the eye cornea provides a scale to convert the measured dimensions to the actual ones. Correction is required with a conversion factor because the projected image as photographed is flat whereas the actual ocular surface is convex.

Alternative to this conventional practice for determining the exposed surface area of the eye is a simpler and faster measurement that stems from the realization that there is a linear correlation between the palpebral aperture and the surface area of the exposed eye. FIG. 1 shows this correlation with a linear-scale plot of palpebral aperture, i.e. central or mid-point lid opening, against the corresponding eye surface area. The straight line curve 10 in this Figure results from the plot of the corrected area of the exposed eye surface as conventionally determined plotted against the measured palpebral aperture. The correlation which FIG. 1 shows between the two parameters is exceedingly close. This finding enables one to determine the area of the exposed surface of an eye, from which evaporation takes place and for other purposes, in a simple and straightforward manner directly from a measurement of the palpebral aperture. This height is readily measured; for example, by viewing the subject's eye through a scale on a lens of the goggle, which locates the scale at a prescribed distance in front of the eye.

The instrument and procedure which the invention thus provides enable persons with relatively little skill to make accurate and precise measurements of tear film evaporation. The instrument and procedure provide controlled and repeatable conditions for the measurement, and the conditions can be near the physiologic condition of the subject. Further, the measurement can be made with minimal discomfort or risk to the subject. The resultant data correlates well with the ophthalmic health of the subject.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention is indicated in the claims.

For a fuller understanding of the nature and objects of the invention, reference should be had to the following detailed description, taken in connection with the accompanying drawings, in which.

DESCRIPTION OF ILLUSTRATED EMBODIMENT

Figure 1:
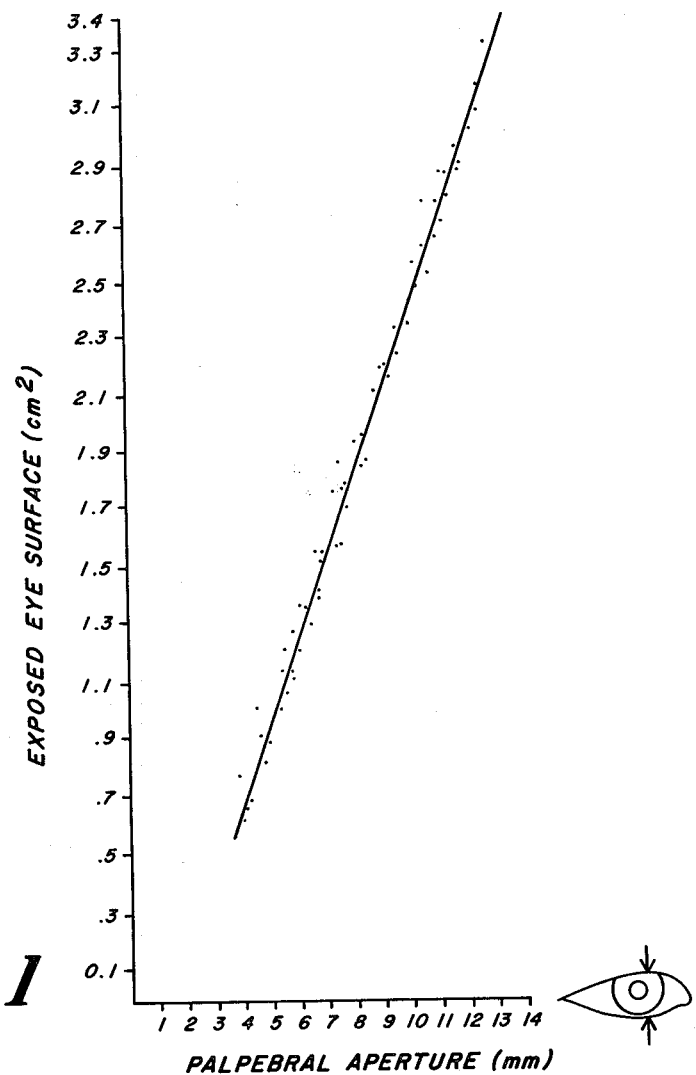
FIG. 1 is a graph showing the relationship between palpebral aperture and exposed surface area as found in accordance with one aspect of the invention.
Figure 2:
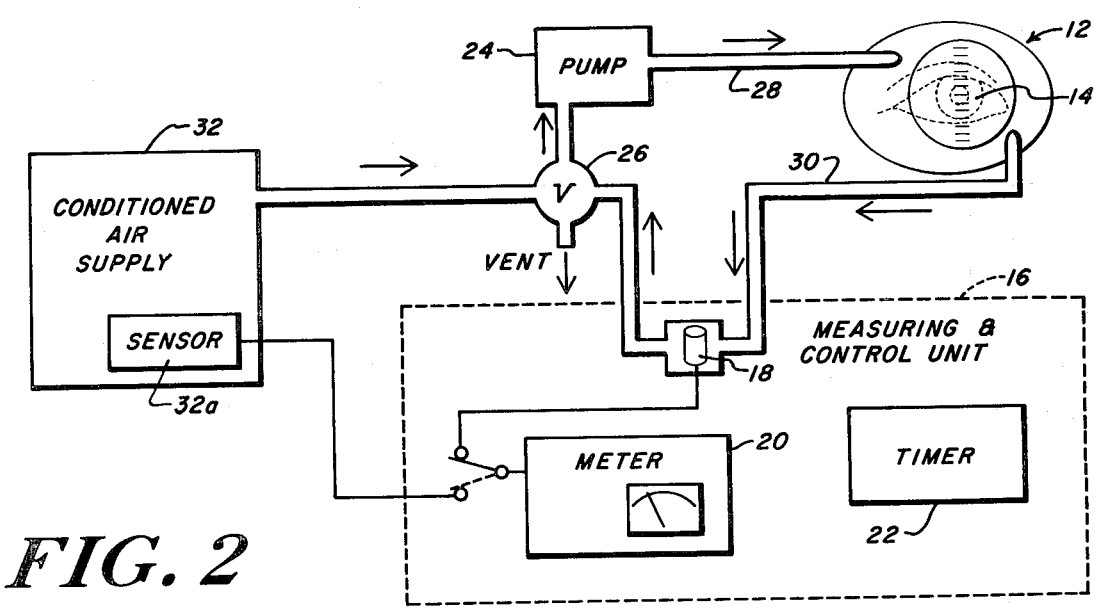
FIG. 2 is a schematic representation, partly in block form, of measuring equipment according to another aspect of the invention.

The illustrated tear evaporation instrument according to the invention has three basic units, as shown in FIG. 2. One unit is a goggle-like eye chamber 12 which fits over a subject's eye 14. A measuring and control unit 16 includes a temperature and humidity-sensing element 18, a meter 20, and a timer 22. There is also a fluid processing unit which includes a pump 24, a valve 26, and inlet and outlet conduits 28 and 30. The conduits interconnect the chamber 12 with the pump 24 and the valve 26, as shown. The illustrated fluid processing unit further includes a supply 32 of conditioned air connected with one input port of the valve 26. The air outlet conduit 30 connects from the eye chamber 12 to a further input of the valve 26. The sensing element 18 is mounted for exposure to air within the outlet conduit 30 as illustrated. One outlet port of the valve 26 is a vent open to the atmosphere and the other outlet port feeds to the pump 24. The air inlet conduit 28 connects from the output of the pump to the eye chamber 12.

Figure 3:
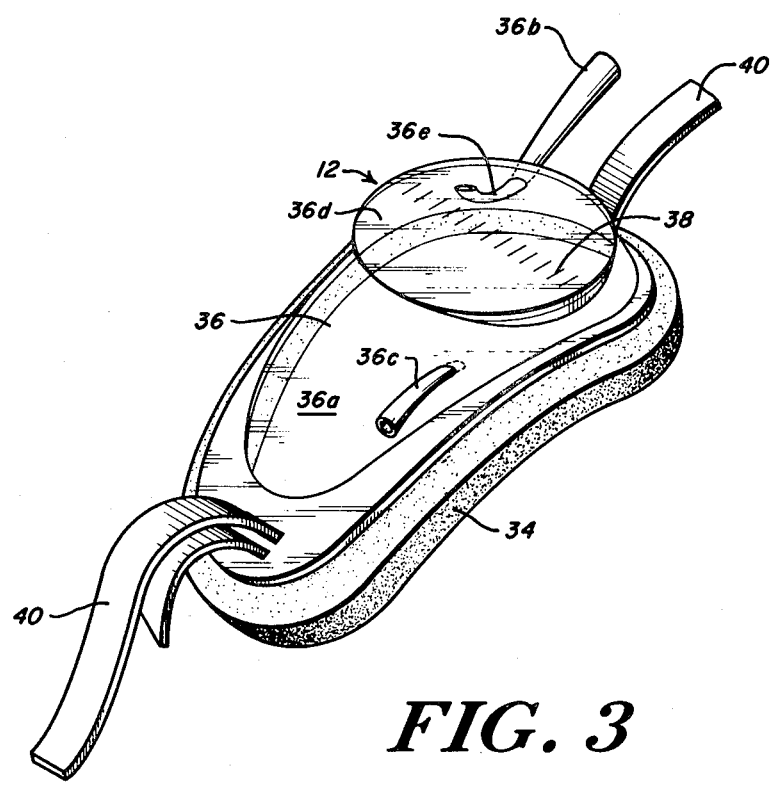
FIG. 3 is a perspective view showing a goggle-like device for use in the equipment of FIG. 2 for practice of the invention.

The illustrated eye chamber 12 has an overall shape and construction similar to that of one eyepiece of a conventional swimmer's goggle. In particular, as FIG. 3 shows, the eye chamber illustrated has an annular sponge-like cushioning seal 34 for seating on the subject's face peripherally about the eye. The cushion carries a goggle dome 36 that, together with the cushion, forms a chamber of substantially known volume over a subject's eye. The goggle dome 36, preferably of optically-transparent material, has a peripheral sidewall 36a apertured with two tubes 36b and 36c for connection with the air conduits 28 and 30, respectively. A lens 36d, illustrated as flat, forms the top of the dome 36. A series of graduations forming a scale 38 for measuring the palpebral aperture is engraved or otherwise marked on the lens 36d.

The illustrated tubes 36b and 36c are located diametrically opposite one another on the dome wall 36a, and the inlet tube 36b extends through the dome wall to a nozzle 36e that is curved to direct air exiting from it against the lens 36d and hence away from the eye of a subject on which the eye chamber is fitted. This inwardly-projecting nozzle 36c is considered preferable to avoid directing air onto the eye of a subject. Instead, the air flow moves primarily laterally relative to the eye of a subject. The opposed orientation of the two tubes is considered desirable to enhance moving all air within the chamber, for initializing the chamber and for mixing the air therein prior to measurement.

A head strap 40 affixed to the goggle dome 36 holds the eye chamber 12 securely in place over a subject's eye.

Referring again to FIG. 2, which shows the eye chamber 12 of FIG. 3 in place over a subject's eye 14 with the inlet conduit 28 attached to the inlet tube 36b and the outlet conduit 30 attached to the outlet tube 36c, the valve 26 and control unit 16 can provide either of three conditions of the air or other gaseous fluid within the chamber and the fluid processing portion of the instrument.

To prepare the instrument for use, the valve is set to direct conditioned air, i.e. air of a known temperature and humidity and hence of known relative humidity, from the supply 32 to the pump 24, which is on, for delivery to the chamber 12 via the inlet conduit 28. The valve 26 in this position connects the chamber outlet conduit 30 to the vented valve port. With this arrangement, conditioned air from the supply 32 fills the chamber and the valve 26, pump 24, and conduits 28 and 30. The meter 20 of the measuring and control unit 16 measures the humidity-responsive signal output from the sensing element 18 during this condition to monitor when the measured relative humidity is at the selected base line condition desired preparatory to a measurement. In one illustrated practice of the invention, the conditioned air supply 32 provides air with a humidity of 23% at a temperature of 24° C. This conditioned air is flushed through the instrument until the meter 20 indicates that the relative humidity as measured with the sensing element 18 attains a level of around 29%.

The valve 26 is then switched to interconnect the outlet conduit 30 with the inlet conduit 28, and the pump continues to operate to ensure that the fluid path thus provided, including the eye chamber 12, is uniformly at the selected initializing relative humidity condition. During this preparatory operation, as indicated above, the eye of the subject is closed and the vaseline jelly previously applied to the subject's eyelid and other skin surrounding the eye essentially prevents evaporation from the subject into the eye chamber 12.

In the next operating step, the valve 26 is maintained in the position where it interconnects the air conduits 28 and 30, the pump 24 is turned off, and the timer 22 started for timing an evaporation interval during which the eye 14 of the subject is maintained open. The width of the lid aperture is measured using the scale 38 on the chamber lens 36d. The evaporation interval in one instance is one minute, after which the subject closes the eye 14 and the pump 24 is again turned on. The air flow from the pump through the inlet conduit 28 to the eye chamber 12 and out the outlet passage 30 and through the valve 26 and back to the pump mixes the air within the eye chamber to provide a uniform humidity level throughout the contained volume through which the air circulates. A measurement of this relative humidity by way of the sensing element 18 and the meter 20 thus measures a sample of the mixed air, which now includes water vapor which evaporated from the eye of the subject during the evaporation interval.

With the relative humidity values thus measured before and after an evaporation interval in this manner, the evaporation rate is determined as described above with reference to equation 3. The volume, V, in equation 3 is the volume of the eye chamber 12, pump 24, valve 26 and conduits 28 and 30, i.e. the volume through which air circulates for the post-evaporation mixing step.

In one embodiment, the measuring and control unit 16 includes a microprocessor for automatically calculating the evaporation rate. Such an automated measuring and control unit 16 typically controls the pump 24 and includes a drive element for automatically placing the valve 26 in the desired position for each step of the instrument operation. The further automation and construction of the measuring and control unit 16 is well within the skill of the art and is not described further. Further, the sensing element 18 typically includes two subelements, as conventional; one for sensing humidity and another for sensing temperature.

FIG. 2 also illustrates an optional sensing element 32a for sensing the humidity and temperature of the air which the supply 32 delivers. A single-pole, double-throw switch can be provided to connect either this optional sensing element or the sensing element 18 to the meter 20, as illustrated.

The foregoing evaporation measuring instrument was used on human subjects, both with normal eye tear films and with pathologic tear film conditions. The average evaporation rate measured in normal eyes was $4.07 \times 10^{-7} \pm 0.40 \times 10^{-7}$ grams per centimeter squared per second. An average evaporation rate from subjects with pathologic eyes, considered as a group, was nearly double the foregoing value. In further tests with the same subjects but using different palpebral apertures, and consequently different anterior surface areas, the instrument demonstrated that, as expected, the amount of evaporation increases with the eye surface area in a regular predictable way.

A practice of this invention considered preferable employs a conditioned air supply 32 (FIG. 2) that provides a base line humidity which is only slightly below the physiological condition. This is in contrast to employing a highly dry base line condition, which is deemed disadvantageous because it elicits blinking by the subject and simulates an excessive evaporation rate. It is for this reason that one illustrative embodiment provides conditioned air to attain a base line condition within the eye chamber 12 of 29.5% relative humidity, at 23° C.

The preferred embodiment further includes a fluid processing unit and an eye chamber that enhance mixing of air as the pump 24 circulates it through the chamber 12 and conduits 28 and 30, after the evaporation interval. Accordingly, a preferred pump 24 moves air with a pulsating or other turbulent action as is achieved, for example, with a vibratory or pulsating pump mechanism. The illustrated eye chamber 12, FIG. 2, has an irregularly shaped dome 36, which also is considered to enhance a mixing, turbulent flow therein.

It will thus be seen that the equipment and procedure described hereinabove efficiently attain the foregoing objects. The invention provides an instrument and procedure for determining eye surface area from a single scalar measurement, and for determining tear film evaporation rate in a manner which is highly reproducible and which avoids contact with the surface of the eye or the tear film. Since certain changes may be made in the above construction and practices without departing from the scope of the invention, the practice of the invention is not limited to the foregoing specific description. Rather, the description is to be interpreted as illustrative.

The following claims are intended to cover all generic and specific features of the invention described herein, and all statements of scope of the invention which, as a matter of language, might be said to fall therebetween.

Having described the invention, what is claimed as new and secured by Letters Patent is:

1. Apparatus for the non-invasive measurement of evaporation from an eye, said apparatus comprising A. enclosure means for placement over an eye being measured and for forming a chamber thereover substantially closed to the environment,
   B. means for measuring the relative humidity of gaseous fluid, and
   C. fluid processing means selectively operable for allowing gaseous fluid within said chamber to be substantially stationary during an evaporation period, and alternatively for mixing gaseous fluid within said chamber and for exposing said measuring means to at least a sample of said mixed fluid.

2. Evaporation measuring apparatus according to claim 1 in which said fluid processing means includes
   A. means forming a fluid passage connected with said enclosure means for fluid communication with the chamber formed thereby, and
   B. motive means connected with said passage for selectively moving gaseous fluid between said passage and the chamber formed by said enclosure means, thereby to effect said mixing.

3. Evaporation measuring apparatus according to claim 2, further including means disposing said measuring means for exposure to gaseous fluid within said passage, thereby to expose said measuring means to at least a sample of said mixed fluid.

4. Evaporation measuring apparatus according to claim 1 in which said fluid processing means includes supply means for introducing gaseous fluid of selected temperature and selected humidity to the chamber formed by said enclosure means prior to said evaporation period.

5. Evaporation measuring apparatus according to claim 1 in which said fluid processing means includes
   A. means forming a fluid passage connected with said enclosure means for fluid communication with the chamber formed thereby,
   B. motive means for selectively moving gaseous fluid through said passage,
   C. means for introducing gaseous fluid of selected temperature and selected humidity to said fluid passage, and
   D. means disposing said measuring means for exposure to gaseous fluid within said passage.

6. Evaporation measuring apparatus according to claim 1 further comprising means for providing a measure of the exposed surface area of the eye being measured.

7. Apparatus for tear evaporation measurement comprising
   A. goggle-like means adapted for placement over an eye and for forming thereover a chamber substantially closed to the environment,
   B. an air inlet conduit and an air outlet conduit, each of which is connected with said goggle means for communication with the chamber formed thereby,
   C. pump means connected with at least one said conduit,
   D. means for sensing the humidity and the temperature of air exposed to tear-film evaporation within the chamber formed by said goggle means,
   E. measuring means connected with said sensing means for providing a measure of said sensed humidity and of said sensed temperature, and
   F. control means for actuating said pump means for moving air between said conduits and the chamber formed by said goggle means and alternatively for inactivating said pump means during an interval in which said tear film evaporation occurs.

8. Apparatus according to claim 7, further comprising nozzle means on said inlet conduit and projecting within said goggle means for introducing air to the chamber formed by said goggle means with a flow selected for mixing air within said chamber.

9. Apparatus according to claim 7, further comprising nozzle means on said inlet conduit and projecting within said goggle means for introducing air to the chamber formed by said goggle means with a flow selected for mixing air within said chamber, and for engaging the exposed surface of the eye being measured primarily only laterally.

10. Apparatus according to claim 7, further comprising means for delivering to said inlet conduit air with known temperature and humidity.

11. Apparatus according to claim 10, further comprising valve means connected with said conduits and arranged with said control means for selectively admitting air of known temperature and humidity to the chamber formed by said goggle means by way of said inlet conduit and for venting said chamber by way of said outlet conduit, and, separately, for closing said inlet and outlet conduits with said pump means being disabled whereby air within said chamber is substantially stationary, and, separately, for circulating air between said conduits and said chamber for mixing air within said chamber and for exposing said sensing means to said mixed air.

12. Apparatus according to claim 7 in which said inlet conduit and said outlet conduit communicate with said goggle means at substantially diametrically opposite locations.

13. Apparatus according to claim 7 further comprising scale means carried on said goggle means for the measurement of the palpebral aperture of the eye being measured.

14. A method for the non-intrusive measurement of evaporation from an eye, said method comprising the steps of
   A. providing over an eye being measured a chamber substantially closed to the environment and adapted for enclosing gaseous fluid over the eye,
   B. providing substantially stationary gaseous fluid in said chamber for an evaporation interval,
   C. mixing the gaseous fluid within said chamber after said evaporation interval, and
   D. determining the change which occurs during said evaporation interval, of relative humidity of the gaseous fluid within said chamber, said determination including measuring the relative humidity of the mixed gaseous fluid.

15. A method according to claim 14 in which said mixing step includes circulating through said chamber gaseous fluid from outside said chamber.

16. A method according to claim 15 in which said change-determining step includes sensing parameters of gaseous fluid circulated through said chamber at a location external to said chamber.

17. A method according to claim 14 comprising the further steps of
   A. determining the volume of the space in which said gaseous fluid is mixed, and
   B. determining the area of the exposed surface of the eye being measured.

18. A method for the non-intrusive measurement of evaporation from an eye, said method comprising the steps of
   A. providing over an eye being measured a chamber substantially closed to the environment,
   B. allowing gaseous fluid within said chamber to be closed from flow into and out of said chamber for a selected evaporation interval,
   C. mixing the gaseous fluid in said chamber after evaporation during said interval into the chamber from the eye being measured, and
   D. determining the change in relative humidity of the gaseous fluid within said chamber during said evaporation interval.

19. A method for the non-intrusive measurement of evaporation from an eye, said method comprising the steps of
   A. providing over an eye being measured a chamber substantially closed to the environment,
   B. providing in said chamber air of known temperature and humidity condition prior to an evaporation interval,
   C. allowing gaseous fluid within said chamber to be closed from flow into and out of said chamber for an evaporation interval of selected duration,
   D. mixing the gaseous fluid within said chamber after evaporation, during said evaporation interval, into the chamber from the eye being measured, and
   E. determining the change in relative humidity between said known initial conditions and the conditions after said evaporation interval and said mixing.

* * * * *